(12) United States Patent
Halbert

(10) Patent No.: US 12,019,015 B1
(45) Date of Patent: Jun. 25, 2024

(54) DEVICES FOR INDEPENDENTLY-CONTROLLABLE, MULTI-CHAMBER CUVETTES FOR RAPID, CONCURRENT SPECTRAL ANALYSES, EMBODIED APPLICATIONS OF SAME, AND METHODS THEREIN

(71) Applicant: Daniel N. J. Halbert, Bal Harbour, FL (US)

(72) Inventor: Daniel N. J. Halbert, Bal Harbour, FL (US)

( * ) Notice: Subject to any disclaimer, the term of this patent is extended or adjusted under 35 U.S.C. 154(b) by 0 days.

(21) Appl. No.: 18/372,073

(22) Filed: Sep. 23, 2023

(51) Int. Cl.
| | |
|---|---|
| G01N 21/35 | (2014.01) |
| B01F 31/24 | (2022.01) |
| G01N 1/38 | (2006.01) |
| G01N 1/42 | (2006.01) |
| G01N 1/44 | (2006.01) |
| G01N 21/01 | (2006.01) |
| G01N 21/3563 | (2014.01) |
| G01N 21/3577 | (2014.01) |
| G01N 33/14 | (2006.01) |
| B01F 101/23 | (2022.01) |
| G01N 27/06 | (2006.01) |

(52) U.S. Cl.
CPC ......... *G01N 21/3577* (2013.01); *B01F 31/24* (2022.01); *G01N 1/38* (2013.01); *G01N 1/42* (2013.01); *G01N 1/44* (2013.01); *G01N 21/01* (2013.01); *G01N 21/3563* (2013.01); *G01N 33/146* (2013.01); *B01F 2101/23* (2022.01); *G01N 27/06* (2013.01); *G01N 2201/129* (2013.01)

(58) Field of Classification Search
CPC .............. G01N 21/3577; G01N 21/01; G01N 21/3563; G01N 1/38; G01N 1/42; G01N 1/44; G01N 33/146; G01N 27/06; G01N 2201/129; B01F 31/24; B01F 2101/23
See application file for complete search history.

(56) References Cited

U.S. PATENT DOCUMENTS

2015/0315631 A1* 11/2015 Handique ............ C12Q 1/6806
506/26

* cited by examiner

*Primary Examiner* — Jamil Ahmed
(74) *Attorney, Agent, or Firm* — Reuven K. Mouallem; FlashPoint IP Ltd.

(57) ABSTRACT

The present invention discloses devices for independently-controllable, multi-chamber cuvettes for rapid, concurrent spectral analyses, embodied applications of same, and methods therein. Devices include: a multi-chamber cuvette having contiguous analysis chambers forming a single continuous inner cavity configured to contain a liquid in an inner-cavity volume, wherein each chamber is configured to serve as a measurement zone for the liquid in the inner cavity when the volume is filled with the liquid by regulation of hydrostatic pressure in the inner cavity in order to prevent fluid flow from a given chamber to another chamber, and wherein each volume in each zone is designated a zone volume; thermal-contact windows positioned in a chamber to enable independent temperature control of a zone volume in a zone; and cuvette optical windows, positioned in each chamber to provide independent optical access to each zone, adapted to enable analysis of each zone volume in each zone.

7 Claims, 7 Drawing Sheets

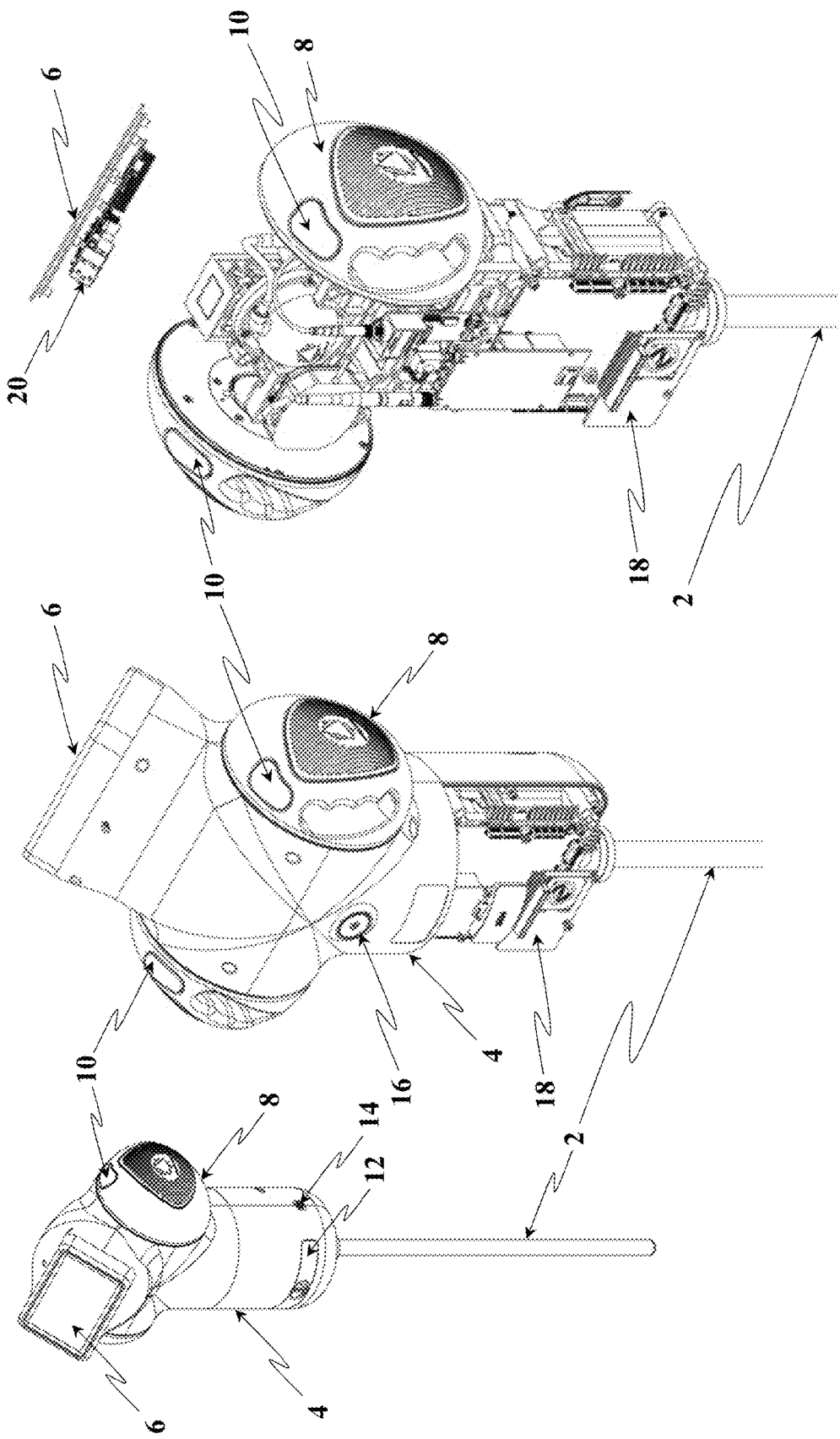

Exemplary Embodiment

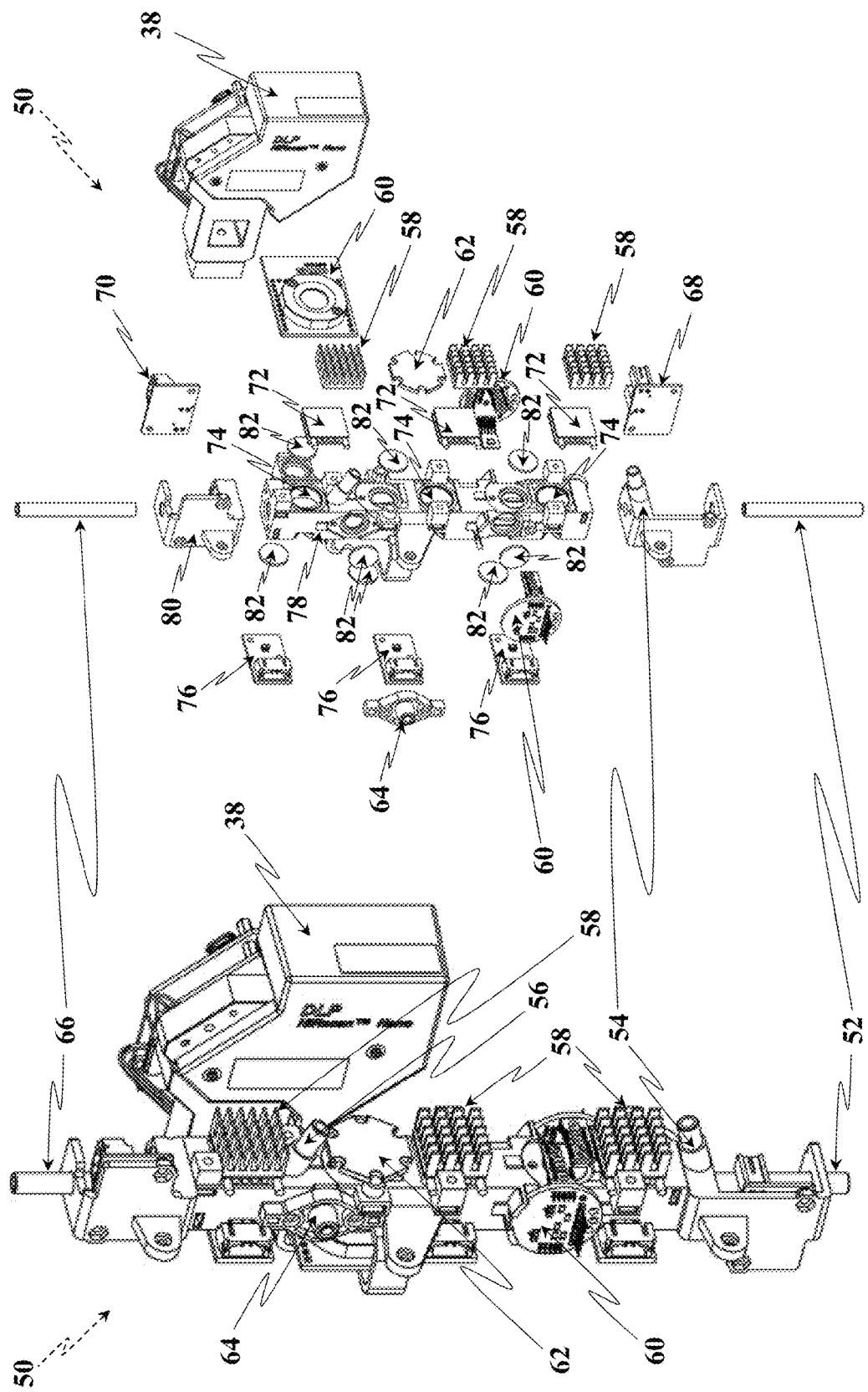

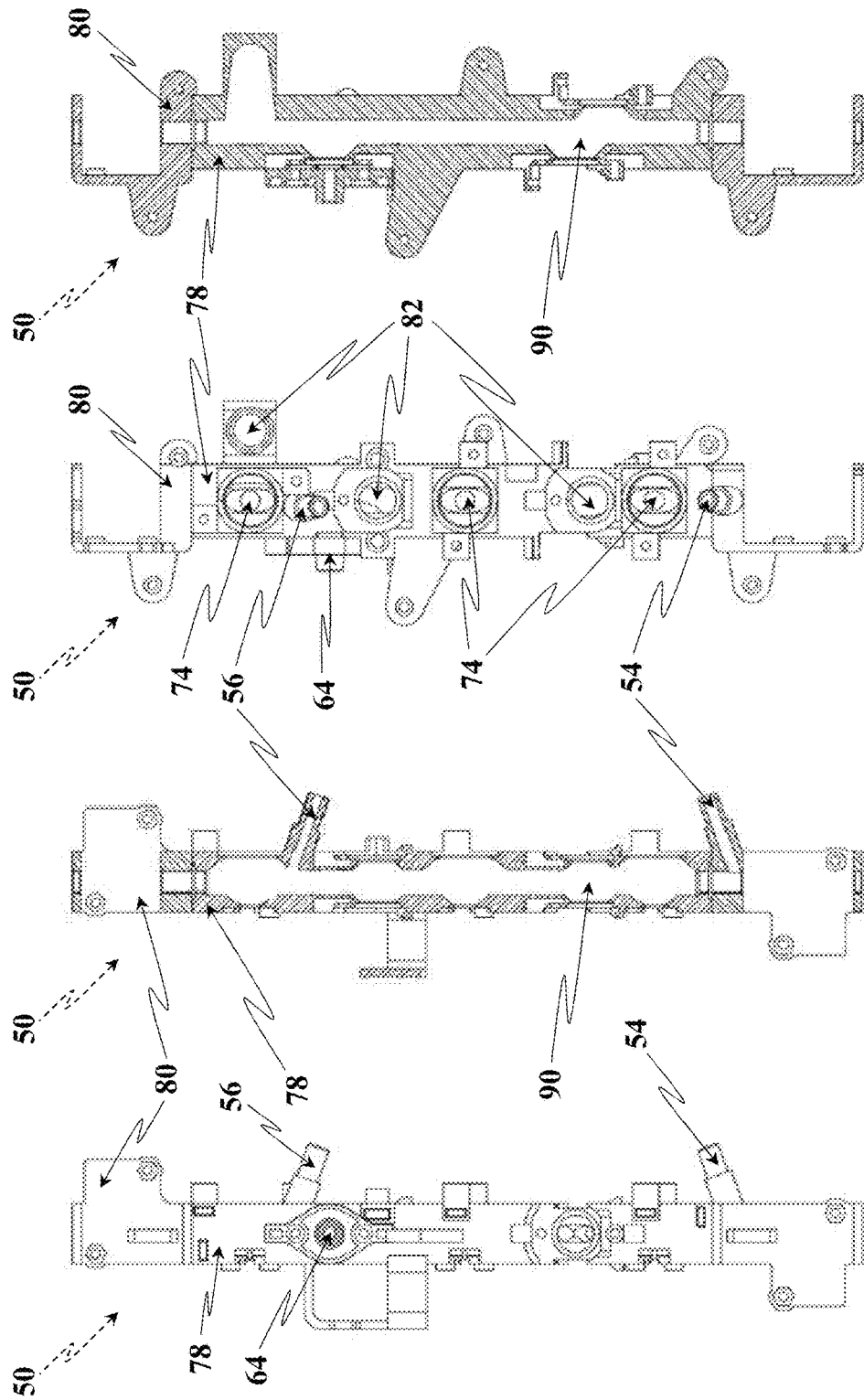

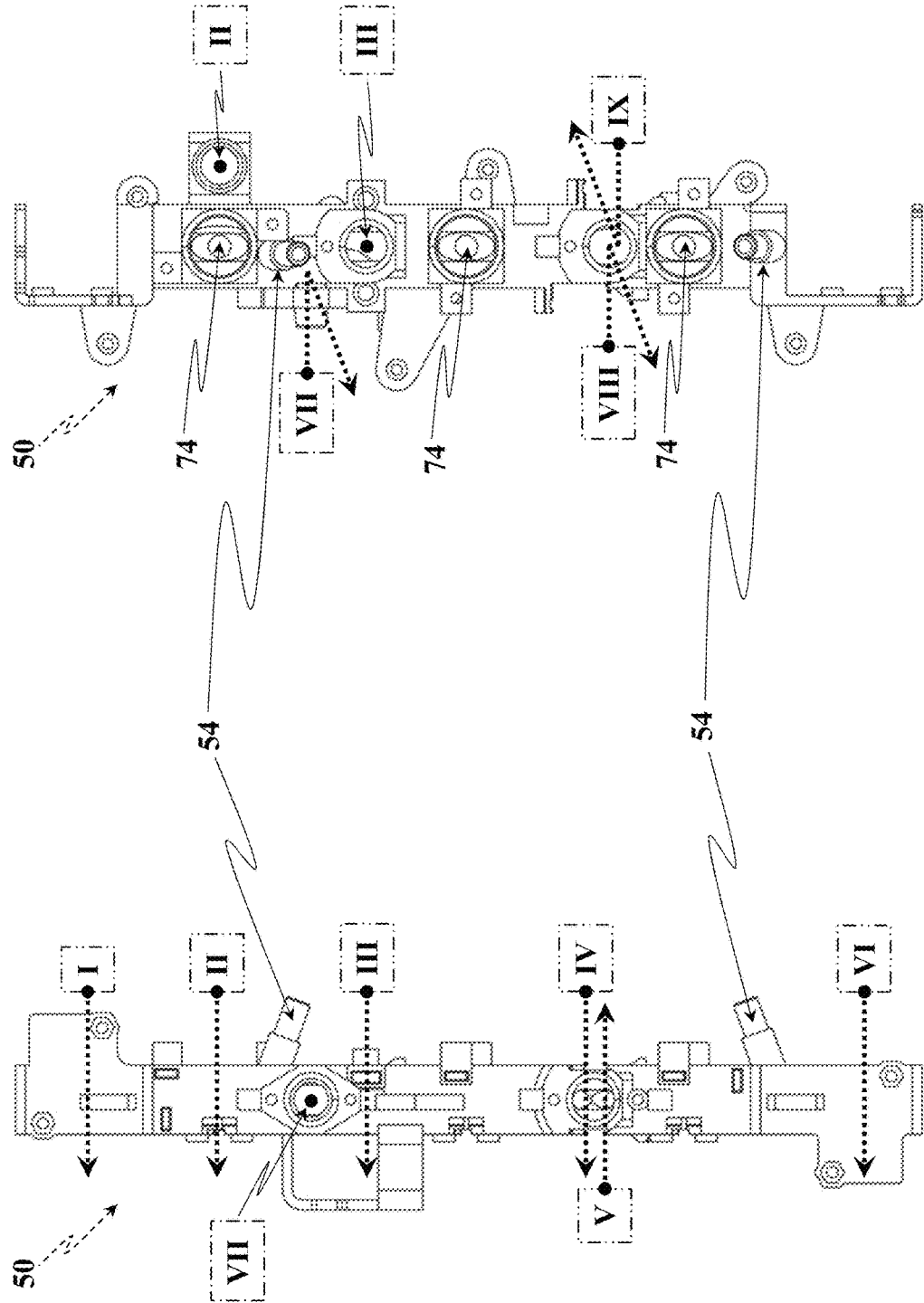

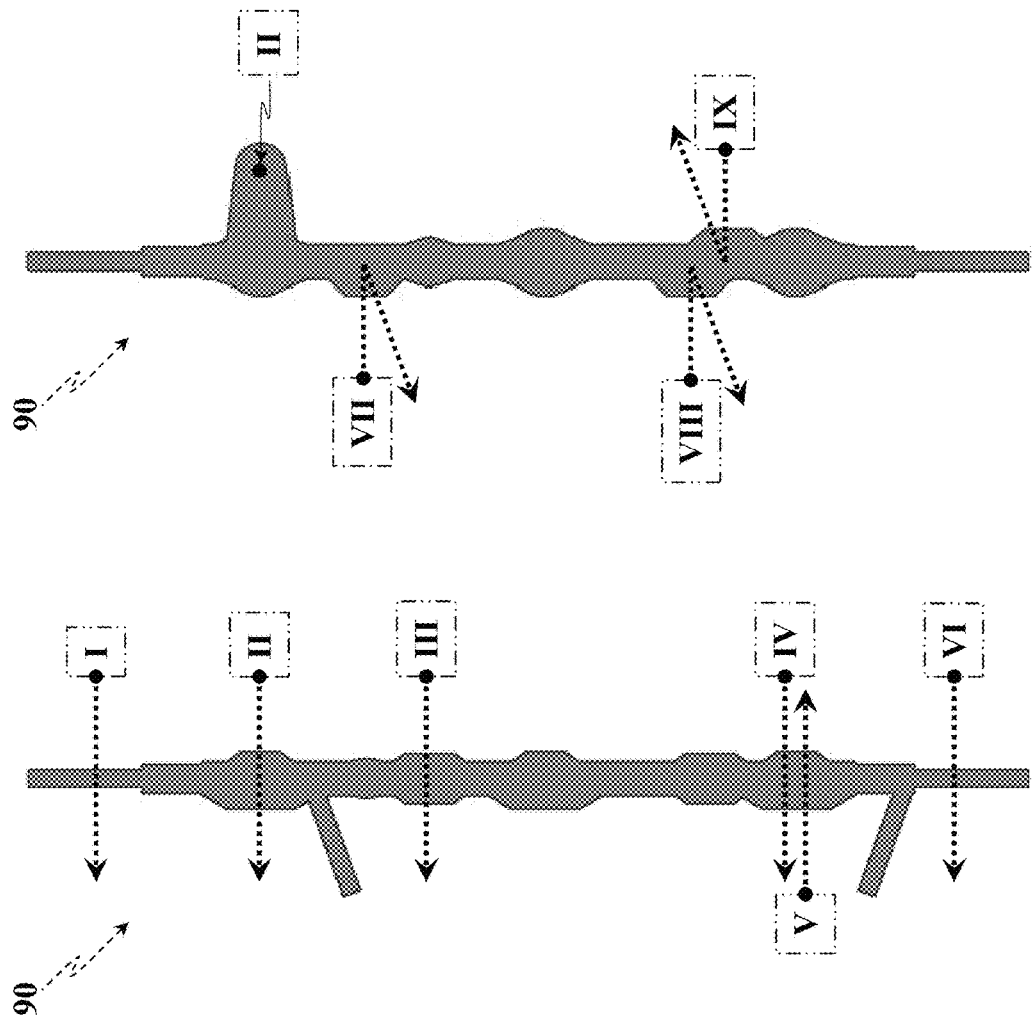

DEVICES FOR INDEPENDENTLY-CONTROLLABLE, MULTI-CHAMBER CUVETTES FOR RAPID, CONCURRENT SPECTRAL ANALYSES, EMBODIED APPLICATIONS OF SAME, AND METHODS THEREIN

FIELD AND BACKGROUND OF THE INVENTION

The present invention relates to devices for independently-controllable, multi-chamber cuvettes for rapid, concurrent spectral analyses, embodied applications of same, and methods therein. In particular, the present invention relates to the embodied applications in the fields of agriculture, plant growth methodology, and plant development regulation. In one application, in-field monitoring of all stages of wine production is enabled via analyses of grape, soil, and barrel wine, and wine aging parameters, as well as quality control of bottled wine production—information important to wine growers, winemakers, winery managers and owners, and wine consumers. Another application includes broader food and beverage monitoring for quality control and health safety relating to spoilage. Another application relates to fuel monitoring for quality and regulatory compliance.

To illustrate the need for such devices, the application of in-field monitoring of the various stages of wine production is detailed below to highlight the multitude of parameters affected during the maturation and industrial production of wine. Such elaboration would equally apply to other applications as mentioned above and discussed further in the description of the embodiments.

Wine is a complex mixture of water, alcohol, and a significant amount of organic and inorganic substances. The complexity and variability of wine content presents the main challenge for the majority of winemaking processes, starting from the production of wine from must (i.e., freshly crushed fruit juice that contains the skins, seeds, and stems of the fruit) to the processes of aging. Some processes of wine storage and aging are accompanied by a significant reduction in wine stability and/or consumer properties (e.g., spoilage). Physical spoilage mostly consists of the delayed instability of the solubility of potassium and calcium salts of tartaric and malic acids—depending on the temperature, pH, acid content, and alcohol content of the wine. This process may lead to the instant or delayed formation of residue either in a dense crystal form or as an opaque impurity. Such processes may also involve defects with the glass wine bottle leading to the formation of residue or opacity—formed by the inorganic silicates.

Microbial spoilage is one of the most significant ways wine spoils. It can be easily identified by an increase in the content of acetic acid and wine acidity during the acetic fermentation process caused by *Acetobacter* and some other bacterial species. Delayed and other fermentation processes may also lead to spoilage. For example, malolactic fermentation caused by *Lactobacillus* or other bacterial species may increase the formation of biogenic amines. One of the most noticeable types of this spoilage includes the action of the Brettanomyces species causing an off-flavor of wine. Another noticeable example is a cork taint from Trichloroanisole (TCA) formation by fungal strains. Chemical spoilage involves processes of deesterification/reesterification (e.g., increased formation of acids, alcohols, and esters), oxidation (e.g., increased formation of acids and aldehydes, the decay of phenolic substances), decarboxylation (e.g., a noticeable increase of sulfur-containing compounds and amines), and other processes involving both macro- and micro-components of wine.

Some forms of undesired wine spoilage processes can be reduced by appropriate grape-handling and winemaking procedures during the various stages of wine preparation. For example, a grape planted in the most optimal conditions for the desired level of organic and amino acid content may be processed into the wine with a proper cold treatment supported by controlled malolactic fermentation to improve acid content. Furthermore, oxygen-free storage, filtration, and other processes accompanied by proper bottling will lead to a reproducible, high-quality wine. Ideally, a proper winemaking production process should lead to wine being subject only to the aging process. The storage of bottled wine may affect the spoilage as well. Recommended wine storage conditions include storing wine at the following temperatures: for example, red wine requires between 12-19° C.; white wine requires between 8-12° C.; and champagne requires between 5-8° C. Humidity should generally be kept between 50-80% and in a dark environment. Each bottle should be stored on its side to avoid drying out the cork inside.

But the situation with any wine changes when the bottle is opened, leading to increased oxygen saturation and contamination with the local microbiome. Sometimes the wine may also be affected by sunlight and warm or hot temperatures. This situation may lead to increased spoilage processes, mostly microbial and chemical. The process of wine spoilage may lead to the alteration of the content of many wine constituents, including gaseous components, and can include acetic fermentation. Acetic acid is volatile, so its presence is relatively easy to track due to the significant amount of produced acid. Fermentation by Brettanomyces can lead to noticeable changes in the wine due to volatile phenolic compounds and isovaleric acid with relatively significant concentrations. Corks tainted by TCA and/or other haloanisole compounds are a significant problem due to the olfactory senses of the nose being sensitive to them. Various sulfur compounds obtained from amino acids may give a wide range of undesired odors (e.g., rubber, potato), and be present in a high range of concentrations (e.g., up to milligrams per liter) with different odor thresholds. Diacetyl formation by lactic bacteria may lead to caramel or butter tones depending on the concentration.

The most significant problem facing wine spoilage products is the lack of approved regulations for the majority of these compounds. For example, the International Organization of Vine and Wine (OIV) only recommends limiting acetic acid below 1.2 grams per liter. Meanwhile, the compendium of recommended analytical methods for wine analysis contains detection procedures for most mentioned undesired substances. Most of the modern and highly used methods of wine analysis are very sophisticated in terms of sensitivity, speed, number of traced components (e.g., gas and liquid chromatography, mass spectrometry, nuclear magnetic resonance). Unfortunately, the majority of analytical methods and devices are too extensive, complicated, and/or costly devices to be utilized for rapid, real-time analyses. Moreover, the operator of such techniques must have significant chemical/technical skills to employ such devices.

Many in the wine industry have started adapting technology to understand wine parameters using sensors. PCT Patent Publication No. WO2007008241A1 and U.S. Pat. No. 9,511,910 teaches wine temperature sensors with digital temperature readouts. PCT Patent Publication No.

WO2015187545A1 discloses a wine sensor having temperature and humidity data collection. PCT Patent Publication No. WO2002033404A2 discloses a means to measure parameters such as acidity, pH, alcohol, and dissolved oxygen using optical methods with scattered light. U.S. Pat. No. 4,490,042 teaches measurement of wine quality constituents for quality. U.S. Pat. No. 10,254,265 teaches employing sensors to detect indications of spoilage in wine.

However, what is needed is a portable, real-time measurement device that can assess a robust set of such parameters (or, in a broader context, a critical set of parameters for any given application). Given that much of the analyses described in the prior art relies on chemical information, spectroscopic analyses offer the widest and most precise array of analytical techniques for fingerprint-type characterization of complex liquid mixtures.

In the prior art, US Patent Publication No. 2017/0138851 discloses a system and method for multi-parameter spectroscopy. U.S. Pat. No. 10,660,557 teaches a system fluid analysis cuvette with coupled transparent windows for determining a concentration of an analyte in a fluid (e.g., blood).

It would be desirable to have devices for independently-controllable, multi-chamber cuvettes for rapid, concurrent spectral analyses, embodied applications of same, and methods therein. Such devices and methods would, inter alia, overcome the various limitations mentioned above.

SUMMARY

It is the purpose of the present invention to provide devices for independently-controllable, multi-chamber cuvettes for rapid, concurrent spectral analyses, embodied applications of same, and methods therein.

It is noted that the term "exemplary" is used herein to refer to examples of embodiments and/or implementations, and is not meant to necessarily convey a more-desirable use-case. Similarly, the terms "alternative" and "alternatively" are used herein to refer to an example out of an assortment of contemplated embodiments and/or implementations, and is not meant to necessarily convey a more-desirable use-case. Therefore, it is understood from the above that "exemplary" and "alternative" may be applied herein to multiple embodiments and/or implementations. Various combinations of such alternative and/or exemplary embodiments are also contemplated herein.

Embodiments of the present invention provide users with a means for portable sampling and testing of a wide array of chemical parameters without the need for large-scale laboratory instruments such as amino-acid testers and enzyme assays. Independently-controllable, multi-chamber, interchangeable cuvettes allow for multiple sensors to be installed in the analyzer when conducting various tests, equipping the cuvettes with any number of chambers according to the application requirements. Analyzers employing such cuvettes can be configured to be extremely simple to operate with a clear user interface.

Such analyzers provide portable analytical devices featuring a multitude of sensors that can be selected based on the requirements of the application. Examples of such sensors include: a NIRScan Nano (900-1700 nm) near-infrared (NIR) spectrometer, an AS7261 6-channel visible light sensor, an AS7263 6-channel NIR light sensor, an AS7341 11-channel multispectral sensor unit, an electric conductivity sensor, and an oxygen sensor. Additionally, the analyzers can incorporate a QR-code or other scanner (for sample scan information, user credentials, and/or calibration data for accurate data recording and traceability), GPS location tracking (for recording exact geographical locations of each sample to ensure location-sensitive data accuracy), Peltier heating units (for uniformly heating liquids), an ultrasonic degassing unit (for uniformly degassing liquids samples for reliable, consistent measurements), and an aliquot syringe pump for automated sample processing (i.e., sample collection, internal transfer, analysis, and ejection).

Embodiments of the present invention provide analyzers having modular configurations incorporating independently-controllable, multi-chamber cuvettes that allow for both transmission and reflectance modes for spectral analysis (e.g., using the NIRScan Nano), enabling versatile analysis of liquid and dry samples. Use cases for such analyzers are numerous. Applications include:

(1) Environmental monitoring for rapid, on-site analysis of water quality, soil composition, and pollutant detection, reducing the time and costs associated with traditional laboratory methods.

(2) Agricultural monitoring for farmers, agronomists, and agribusinesses to monitor crop health, soil nutrients, and water resources, optimizing resource allocation and maximizing yield.

(3) Food and beverage industry monitoring for food manufacturers and quality control laboratories to ensure product quality, safety, and regulatory compliance, minimizing production downtime and reducing the risk of product recalls.

(4) Pharmaceutical monitoring for non-destructive testing, quality control, and compliance assurance, streamlining the analytical processing and reducing the need for multiple analytical devices.

For applications in the area of grape cultivation and wine production, users of this device can generally be grouped into grape growers, winemakers, winery managers, and wine consumers. In addition, real-time assessments of parameters grape maturity, wine fermentation, nutritive value, stability forecast, and disease are important, rather than historical analysis obtained from sending samples to off-site (or even on-site) laboratories. An elaboration on the significance and utility of such capabilities, and how they are employed, for the various stakeholders in the wine industry provided below as an exemplary case study of the broad applicability of such multi-chamber cuvettes.

A portable multi-chamber analyzer enables wet and dry field testing to be performed. Such real-time field data facilitates growers and winemakers to collaborate on production strategies in new ways. Typically, grape growers perform most of the physical tasks in the vineyards including planting, trellis maintenance, spraying, and coordinating harvests. Most winemakers tend to be reactive, spending time in the field mainly when a problem is discovered during harvest or grape crushing. The analyzer allows growers to play a greater proactive role in the wine production process by getting ahead of problems before they can manifest through the vineyard, and sharing time-sensitive data with winemakers for feedback in real time (or "semi-real time").

Examples of such time-critical feedback include the measurement of grape sugar and acidity directly in the field in order to evaluate the grape maturity, and estimate the harvesting time with reliable and practical impact on the winemaking process especially due fluctuations due to climate change. Previous historical measurements (e.g., using laboratory testing only) may be only partly usable under such conditions. Another example includes effects on the winemaking process caused by grapes affected by some new perturbing factor (e.g., smoke from forest fires). Historical data may not be available for such a perturbing factor.

Moreover, integrating all analyses into a portable multichamber analyzer reduces costs associated with laboratory testing and the logistics of tracking various results as they are obtained at different times.

For grape growers working in vineyards, such real-time testing helps growers identify problem areas in rows and panels of grape trellises so that corrective actions can be performed quickly before they have a chance to influence yields. For example, while using integrated components to the analyzer (ancillary to the cuvette), solid samples can be assessed to spot-check pH in soils in rows. A grower observing that a row is out of range can add lime to the soil to bring the soil back to proper limits before the row is impacted.

All plants and soil micro-organisms have preferences for soil within certain pH ranges, usually neutral to moderately acid or alkaline. Soil pH most suitable for grapevines is between 5.5 and 8.5. In this range, roots can acquire nutrients from the soil to grow to their potential. As soil becomes more acidic or alkaline, grapevines become less productive. It is important to understand the impacts of soil pH in managing grapevine nutrition, because the mobility and availability of nutrients is influenced by pH.

Acidic soils below pH 6 often have reduced populations of micro-organisms. As microbial activity decreases, nitrogen availability to plants also decreases. Sulfur availability to plants also depends on microbial activity so in acidic soils, where microbial activity is reduced, sulfur can become unavailable. Sulfur deficiency is not usually a problem for vineyards as adequate sulfur can usually be accessed from sulfur applied as foliar fungicides.

Phosphorus availability is reduced at low pH because it forms insoluble phosphate compounds with aluminum, iron, and manganese. Molybdenum is seldomly deficient in neutral to alkaline soils, but can form insoluble compounds in acid soils. In strongly acidic soil (pH<5) aluminum may become freely available to plants at toxic levels. High aluminum levels stunt the growth of roots with detrimental effects on water and nutrient uptake, especially in dry conditions. Iron, manganese, and zinc are more available in acidic soil. In particular, manganese can reach toxic concentrations in acidic soil. Increasing soil acidity can increase the uptake of heavy metals such as copper and lead. This can be a problem in vineyards that have been planted on old apple or pear orchard soils where copper, lead, and arsenic may have accumulated.

Acidification affects soil biology and soil pH values below 5.5 may: impact negatively on nitrogen and carbon turnover; reduce earthworm numbers; change the population dynamics and reduce overall numbers of useful bacteria and fungi. This prevents the breakdown of organic matter to release stored nutrients in forms more available to plants. This can have particular implications for conversion of the various forms of nitrogen applied in nitrogen-based fertilizers.

The best way to detect and monitor soil acidity problems is to conduct regular soil tests—measuring pH is probably the most common soil test used. In irrigated vineyards, care must be taken to sample the vineyard soil from areas and appropriate depths that enable proper interpretation of the analysis results.

Embodiments of the present invention further provide grape growers with metrics to determine harvest dates. The analyzer can perform wet sampling on crushed grapes in the field periodically before harvest to see how the levels of sugar and acids are progressing. A determination to pick grapes can then be based on such sampling. Therefore, it is important that the grape sample data is accurate so that it will reflect the level of maturity or ripeness of the entire crop. It is also important that sample mimic the juice obtained from an actual winery crush. The goal is to have vineyard samples accurately reflect must composition at the winery and in-field testing using the analyzer can achieve this goal.

Potential alcohol content (in the form of sugar) used together with acid content (acid measurement or pH) enables technical maturity to be determined. Maturity of grapes related to pH alone suggests specific pH values for harvesting different cultivars. Acid-containing ratios as indicators of maturity have been commonly applied. Depending on the particular group into which a cultivar falls, and from which area it comes, it would be suitable for either a table or a dessert wine. Some researchers suggest that sugar/acid balance of the grapes in their study was more important, with respect to quality, than the geographical source of the grapes. Indications under conditions of another study were that, in cooler regions, quality of wine was reasonably independent of maturity; whereas, in warmer areas an optimum level of maturity appeared to exist and could be related to sugar/acid ratios of the fruit. So, this factor may become more important due to climate-change effects caused by global warming.

Embodiments of the present invention further provide the ability to link and record field tests with locations in the vineyards with precision. The user sets the location of a vineyard with latitude and longitude coordinates in accordance with global positioning satellites. The analyzer can then communicate with various active and passive IoT devices that emit signals inside the vineyard. For example, after finding a problem with grapes in a panel in a specific row, the grower can return to the panel and perform additional sampling with the analyzer.

Complicating this scenario is the fact that while such sensor devices can measure moisture and/or other soil parameters at the ground level, parameters of the grape itself must be evaluated at the elevated level (e.g., about one meter from the ground). It is hard to power such sensor devices using wires due to the significant area of vineyards, and positioning of solar panels may be complicated in the case of mechanized harvesting. Moreover, such sensor devices must be relocated during the vine covering period. The vine structure may not be able to carry the load of a sensor device, so it must be located on a separate stand or trellis. The sensor positions in the vineyard may require an exact location based on inter alia the field inclination, soil parameters, and light coverage, so the geolocation becomes an important factor.

Winemakers are responsible for maintaining strict quality control during the winemaking process, and generally perform several key steps after grapes are harvested that include crushing, fermentation, clarification (i.e., barrel aging), and bottling. Embodiments of the present invention further provide the ability to test properties of juices in real time to ensure clarity and that appropriate sulfur oxide levels are present. For example, a winemaker can sample must (i.e., crushing juice) to ensure tannins in the skins are not leaching into and spoiling the color of white wine. In extreme cases, the analyzer may detect anomalies in the pressed juices, and subsequently halt production. Winemakers can view harvest data, and trace problem grapes back to locations in the vineyard.

Embodiments of the present invention further enable winemakers to monitor volatile levels during fermentation. The analyzer can be used to sample barrels and vats for continually monitoring how well sugars are being converted into alcohols with ethanol as a conversion indicator. Once such data has been collected over time, and outcomes under various conditions have been determined, winemakers can use the system to predict which fermentation methods best suit their wines. For example, a winemaker may choose to replace an ambient unpredictable yeast with strains of their preference. Over time barrels can be sampled for ethanol (along with sugars, alcohols, and pH) to develop wine yeast profiles for making predictions for future fermentations.

Fermentation volatiles are monitored due to the canonical oenological regulations and mostly include the determination of alcohol and so called "volatile acidity" (mostly presented as acetic acid). Such parameters are important, and have a significant impact on the quality and cost of wine, requiring their control during processing. Other volatile constituents can be analyzed to estimate the overall quality and completeness of operations (e.g., other major alcohols, acids, and esters), and to estimate the potential wine faults and diseases (TCA, phenols, heterocyclics, sulfur, and other compounds). In most situations, only real-time or semi-real time analysis with the shortest possible delay is acceptable.

The selection of yeasts has a significant impact on the wine quality, so it is an important parameter of winemaking. Many industrial-grade yeast strains have undergone a thorough genome profiling and standardization, so they can be applied precisely for various grape varieties, technical conditions (e.g., not enough grape maturity), and desired result. Using retrospective data collected for similar grape varieties, weather conditions, and a current situation considering the newly-defined parameters of a fresh harvest, a winemaker can obtain the best desired results.

Embodiments of the present invention further allow winemakers to perform quality control measures quickly and efficiently in wine cellars during barrel aging. For aging white wines, the analyzer can monitor long-term pH level decreases, and for red wines it can monitor long-term aldehydes to ensure tannins from the barrels are leaching out at acceptable levels.

Current monitoring of pH level as well as other wine parameters during the aging performed using standard laboratory recommendations defined by OIV and other regional/industrial standards. Thus, such monitoring is mostly periodic, and affects only a small batch of wine barrels for huge collections. The sample must be taken to the laboratory to conduct a measurement, and used together with other optional metrics to make a decision regarding the aging process. A winemaker must take another sample of wine to repeat the measurement, or test other constituents in case of complicated/unstable results.

Embodiments of the present invention further enable the monitoring of wine quality during the bottling process. Adverse dissolved oxygen levels in wine during bottling stages can cause discoloration to white wines and flavor degradation to both white and red varietals. Measuring the concentration of dissolved oxygen in wine after bottling is carried out by piercing the cork with a small pickup needle so that the bottle keeps all of the wine inside the bottle, and keeps the ambient oxygen out during sampling. Oxygen level is a highly unstable metric, especially during such technical operations like bottling.

Non-destructive methods that allow winemakers to monitor wines during the production process include inserting the analyzer's collection tube into a wine barrel to collect key information for monitoring the fermentation process in real time to ensure that the quality of the wine is within specific tolerances or to maintain "pre-bottle stability." For example, malolactic fermentation to reduce high levels of malic acid, cold treatment, or application of a deacidifier to reduce the content of tartaric acid. Other situations may include the determination of more complex organic substances like diacetyl, potentially responsible for some wine faults. Real-time monitoring of acetic acid may provide information about the undesired conditions of the fermentation process (e.g., temperature and oxygen level).

Embodiments of the present invention further enable wine producers to identify fermentation trends across wine types within their facilities. For example, a winemaker can use the analyzer to routinely measure long-term, chromatic differences in a variety of wines, determining that the color of white wine in stainless steel vats is lighter than those in oak barrels—resulting in a crisper, brighter flavor. The winemaker then uses this data to make decisions about wine profiles. Chromatic parameters of wine are related mostly to the mix of the phenolic substances of different stability, effected by oxygen, sugar, and other constituents. Such processes are highly specific, and can hardly be understood by relying on historical analysis. Real-time analysis of chromatic parameters of wine supported by the estimation of oxygen and some specific organic constituents may provide a predictor of further color changes.

Embodiments of the present invention further enable geolocation of wine samples at the factory level of industrial wineries. The majority of winemaking operations are spatially-distributed requiring adequate data tracking in the factory to correlate time-sensitive production changes detected in the data. For example, GPS is suitable for vineyard conditions as well as for huge wineries. While RFID works better for the compact conditions of wine cellars and for tagging individual reservoirs. Such tracking may also suffer from technical limitations such as GPS not being detectable in deep cellars, and the limited range of RFID rendering it useless in the field and for big reservoirs. Having a portable analyzer that can sample, analyze, geotag the sampling location, and store (and/or transmit) the data circumvents such constraints.

Embodiments of the present invention further enable marketers, hobbyists, wine enthusiasts, and consumers to understand the chemical profile of how their favorite wines taste once they are opened. For example, a customer opens a bottle of red wine, and begins sampling oxygen levels as a glass of wine interacts with the ambient air. By understanding changing oxygen levels in the wine, one can learn which wines tend to remain aromatic longer while others go flat. Such sampling must include the whole sequence of time-dependent operations affecting the wine contents and measurements (e.g., closed-bottle storage, decantation, and open-bottle storage).

Embodiments of the present invention further enable those in the chemical industry (unrelated to the wine industry) to utilize the analyzer to assess fluids such as fuels, solvents, degreasers, and liquids relevant to the food and beverage industry for applications such as production of biofuels from new source materials, fast checking of solvent/fuel stability during storage operations, and checking and elimination of liquid reagent spoilage in force-majeure situations.

Therefore, according to the present invention, there is provided for the first time a device for rapid, concurrent spectral analyses, the device including: (a) an independently-controllable, multi-chamber cuvette having at least two contiguous analysis chambers forming a single continuous inner cavity configured to contain a liquid in an inner-cavity volume, wherein each analysis chamber is configured to serve as an independently-controllable measurement zone for the liquid in the single continuous inner cavity when the inner-cavity volume is completely filled with the liquid by regulation of hydrostatic pressure in the single continuous inner cavity, when operational, in order to prevent fluid flow from a first given analysis chamber to a second given analysis chamber, and wherein each volume of the liquid in each independently-controllable measurement zone is designated as an independent zone volume; (b) thermal-contact windows, suitably positioned in at least one analysis chamber to provide adequate thermal contact to at least one analysis chamber, adapted to enable independent temperature control of at least one independent zone volume, when operational, in at least one independently-controllable measurement zone; and (c) cuvette optical windows, suitably positioned in each analysis chamber to provide independent optical access to each independently-controllable measurement zone, adapted to enable chemometric and/or spectroscopic analysis of each independent zone volume, when operational, in each independently-controllable measurement zone.

Alternatively, the cuvette optical windows are configured to define more than one optical path in at least one independently-controllable measurement zone.

Alternatively, the device further includes: (d) ancillary device components, wherein the ancillary device components are at least two items selected from the group consisting of: (i) an aliquot-collection tube for collecting and ejecting an aliquot of the liquid into the inner-cavity volume; (ii) a hydrostatic-pressure control mechanism for maintaining the hydrostatic pressure; (iii) a hydrostatic-pressure control actuator for performing the regulation and for actuating movement of the aliquot in the inner-cavity volume; (iv) a lower aliquot-level sensor for determining a lower aliquot level in the inner-cavity volume; (v) an upper aliquot-level sensor for determining an upper aliquot level in the inner-cavity volume; (vi) a degasser for uniformly degassing the aliquot; (vii) at least two heating/cooling elements suitably positioned in each analysis chamber for regulating the independent temperature control in each independently-controllable measurement zone; (viii) at least two heat-exchange radiators suitably positioned in each analysis chamber for regulating the independent temperature control in each independently-controllable measurement zone; (ix) at least one sensor light-guide for performing the chemometric analysis; (x) at least one conductivity sensor for performing the chemometric analysis; (xi) an oxygen sensor for analyzing the aliquot; (xii) at least one spectral sensor unit with parallel-mounted, line-of-sight source and detector for performing the spectroscopic analysis; (xiii) at least one light source for performing the spectroscopic analysis; (xiv) at least two spectral analyzers for performing the spectroscopic analysis; and (xv) a solid-sample analysis compartment for performing the spectroscopic analysis in reflectance mode on solid samples.

Most alternatively, the hydrostatic-pressure control mechanism is a syringe pump and the hydrostatic-pressure control actuator is a syringe-pump linear actuator.

Most alternatively, the movement of the aliquot includes a type of agitated mixing of the aliquot in each independently-controllable measurement zone by rapidly oscillating the hydrostatic-pressure control actuator to create an up-and-down shaking of the aliquot.

Most alternatively, at least two spectral analyzers are independently operational in a near-infrared spectral region in transmission and/or reflectance mode.

According to the present invention, there is provided for the first time a method for performing rapid, concurrent spectral analyses, the method including the steps of: (a) collecting an aliquot of liquid into a multi-chamber cuvette assembly; (b) filling a cuvette inner-cavity volume of the multi-chamber cuvette assembly; (c) internally transferring the aliquot to a degasser chamber body for pre-processing; (d) returning the aliquot to at least two measurement zones of the multi-chamber cuvette assembly; (e) independently controlling aliquot portions in at least one measurement zone by heating, cooling, and/or agitated mixing; (f) processing the aliquot portions in each measurement zone by performing concurrent spectral analyses; (g) ejecting the aliquot from the multi-chamber cuvette assembly; and (h) purging and cleaning the cuvette inner-cavity volume of the multi-chamber cuvette assembly prior to subsequent collection.

These and further embodiments will be apparent from the detailed description and examples that follow.

BRIEF DESCRIPTION OF THE DRAWINGS

The present invention is herein described, by way of example only, with reference to the accompanying drawings, wherein:

FIG. 1A depicts a perspective "front" view of a portable multi-chamber analyzer having an independently-controllable, multi-chamber cuvette for rapid, concurrent spectral analyses, according to embodiments of the present invention;

FIG. 1B depicts a perspective "back" view of the portable multi-chamber analyzer of FIG. 1A with its lower housing removed, according to embodiments of the present invention;

FIG. 1C depicts a perspective "back" view of the portable multi-chamber analyzer of FIG. 1B with most of its housing removed, according to embodiments of the present invention;

FIG. 3A depicts a perspective view of the independently-controllable, multi-chamber cuvette assembly employed in FIGS. 1 and 2 with its housing removed and internal componentry exposed, according to embodiments of the present invention;

FIG. 3B depicts an exploded view of the independently-controllable, multi-chamber cuvette of FIG. 3A with its internal componentry exposed, according to embodiments of the present invention;

FIG. 4A depicts a planar view of the independently-controllable, multi-chamber cuvette assembly of FIG. 3A, according to embodiments of the present invention;

FIG. 4B depicts a planar "cross-sectional cutaway" view of the independently-controllable, multi-chamber cuvette assembly of FIG. 4A with the cuvette inner-cavity volume exposed, according to embodiments of the present invention;

FIG. 4C depicts a planar "90-degree rotated" view of the independently-controllable, multi-chamber cuvette assembly of FIG. 4A, according to embodiments of the present invention;

FIG. 4D depicts a planar "cross-sectional cutaway" view of the independently-controllable, multi-chamber cuvette assembly of FIG. 4C with the cuvette inner-cavity volume exposed, according to embodiments of the present invention;

FIG. 5A depicts the planar view of the independently-controllable, multi-chamber cuvette assembly of FIG. 4A with a schematic representation of the optical paths employed during spectral analyses superimposed, according to embodiments of the present invention;

FIG. 5B depicts the planar view of the independently-controllable, multi-chamber cuvette assembly of FIG. 4C with a schematic representation of the optical paths employed during spectral analyses superimposed, according to embodiments of the present invention;

FIG. 6A depicts a planar "120-degree sector" view of the cuvette inner-cavity volume depicted in FIGS. 4B and 4D with a schematic representation of the optical paths employed during spectral analyses superimposed, according to embodiments of the present invention;

FIG. 6B depicts an alternate, planar "120-degree sector" view of the cuvette inner-cavity volume depicted in FIGS. 4B and 4D with a schematic representation of the optical paths employed during spectral analyses superimposed, according to embodiments of the present invention;

FIG. 6C depicts an alternate, planar "120-degree sector" view of the cuvette inner-cavity volume depicted in FIGS. 4B and 4D, according to embodiments of the present invention;

DESCRIPTION OF THE ILLUSTRATIVE EMBODIMENTS

Figures 2A, 2B, 2C, 2D:
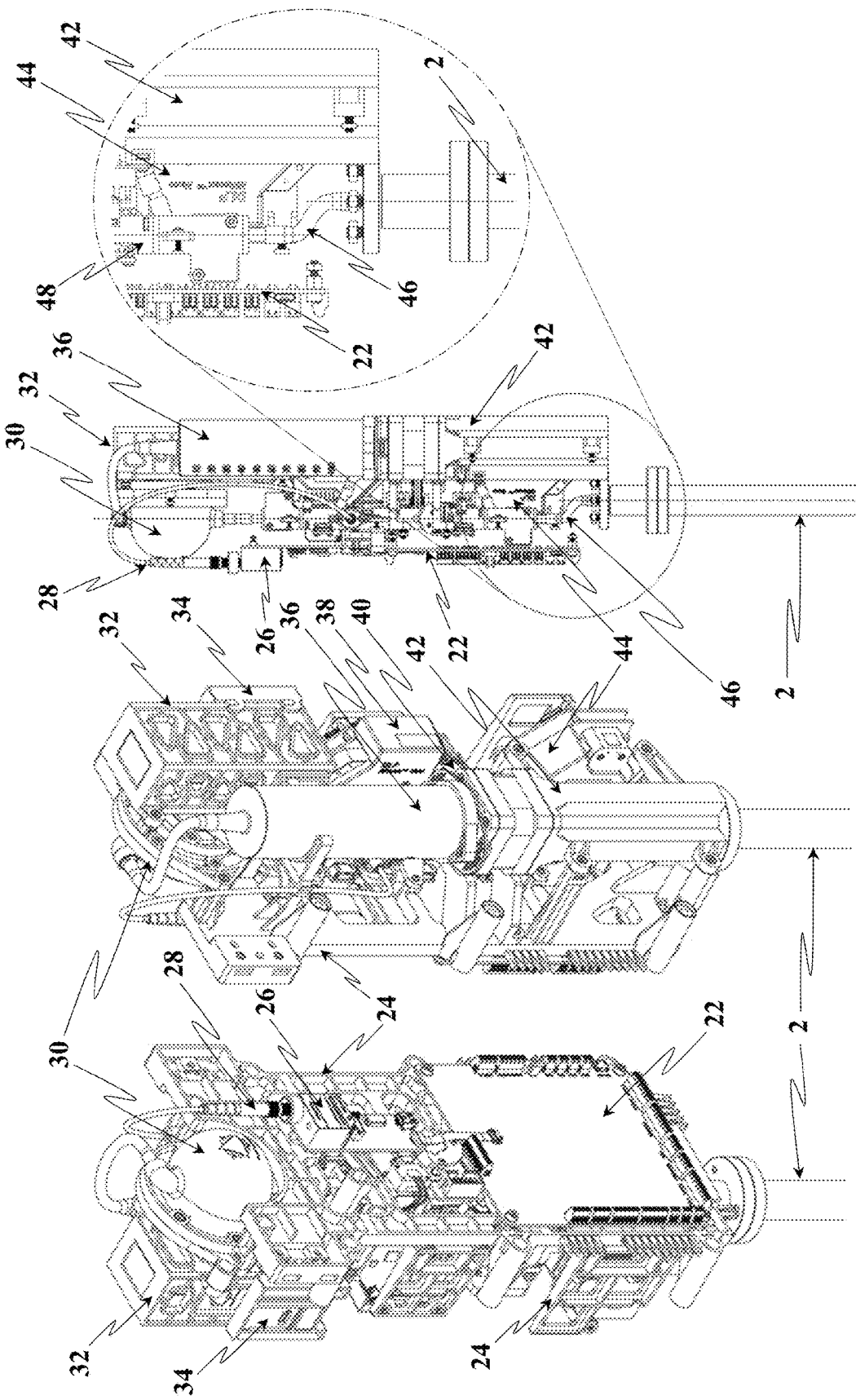
FIG. 2A depicts a perspective "back" view of the portable multi-chamber analyzer of FIG. 1C with its housing removed and internal componentry exposed, according to embodiments of the present invention.
FIG. 2B depicts a perspective "front" view of the portable multi-chamber analyzer of FIG. 2A, according to embodiments of the present invention.
FIG. 2C depicts a perspective "side" view of the portable multi-chamber analyzer of FIG. 2A, according to embodiments of the present invention.
FIG. 2D depicts an exploded view detail of the lower portion of the portable multi-chamber analyzer of FIG. 2C, according to embodiments of the present invention.

The present invention relates to devices for independently-controllable, multi-chamber cuvettes for rapid, concurrent spectral analyses, embodied applications of same, and methods therein. The principles and operation for providing such devices and methods, according to the present invention, may be better understood with reference to the accompanying description and the drawings.

Referring to the drawings, it is noted that FIGS. 1-6 depict different perspective views, different detail views, different planar views, and different magnification views of the same illustrated embodiments. As such, a consistent numbering set is used across the drawings. Identical components depicted in multiple drawings are labelled with the same numbering in all the corresponding drawings.

FIG. 1A depicts a perspective "front" view of a portable multi-chamber analyzer having an independently-controllable, multi-chamber cuvette for rapid, concurrent spectral analyses, according to embodiments of the present invention. The portable multi-chamber analyzer is shown having a multi-capillary aliquot-collection tube 2, a device body 4, a display/selection screen 6 (with a single-board computer, not visible), handles 8, command actuators 10, a solid-sample analysis compartment 12, and a device-charging connector 14.

FIG. 1B depicts a perspective "back" view of the portable multi-chamber analyzer of FIG. 1A with its lower housing removed, according to embodiments of the present invention. FIG. 1B shows the portable multi-chamber analyzer further having a neodymium position-fixing magnet 16 and ancillary components 18 (e.g., Near-Field Communication (NFC) block, a Global Positioning System (GPS) module, and a Subscriber Identity Module (SIM) card compartment).

FIG. 1C depicts a perspective "back" view of the portable multi-chamber analyzer of FIG. 1B with most of its housing removed, according to embodiments of the present invention. FIG. 1C shows the portable multi-chamber analyzer semi-deconstructed with display/selection screen 6 shown having a single-board computer 20, which can be controlled via command actuators 10 and/or other input means (e.g., haptic and voice input).

FIG. 2A depicts a perspective "back" view of the portable multi-chamber analyzer of FIG. 1C with its housing removed and internal componentry exposed, according to embodiments of the present invention. The portable multi-chamber analyzer is shown further having a dedicated controller 22, a support frame 24, an oxygen sensor 26, an oxygen sensor light-guide 28, a degasser chamber body 30, a battery pack 32, and a battery controller 34.

FIG. 2B depicts a perspective "front" view of the portable multi-chamber analyzer of FIG. 2A, according to embodiments of the present invention. The portable multi-chamber analyzer is shown further having an aliquot syringe pump 36, a spectral analyzer 38, a conductivity sensor 40, a syringe-pump linear actuator 42, and a spectral analyzer 44. Depending on the requirements of the application, spectral analyzers 38 and 44 can be units that operate in the NIR range (e.g., NIRScan Nano, AS7261, AS7263, AS7341 operating in transmission and/or reflectance mode).

FIG. 2C depicts a perspective "side" view of the portable multi-chamber analyzer of FIG. 2A, according to embodiments of the present invention. The portable multi-chamber analyzer is shown further having an aliquot-intake cuvette-offset tube 46. FIG. 2D depicts an exploded view detail of the lower portion of the portable multi-chamber analyzer of FIG. 2C, according to embodiments of the present invention. Aliquot-intake cuvette-offset tube 46 can be easily seen connected to the lower portion of a cuvette assembly 48.

FIG. 3A depicts a perspective view of the independently-controllable, multi-chamber cuvette assembly of FIG. 2D with its housing removed and internal componentry exposed, according to embodiments of the present invention. Cuvette assembly 48 of FIG. 2C is depicted in FIG. 3A (with the surrounding structure of the portable multi-chamber analyzer removed) as a multi-chamber cuvette assembly 50. Multi-chamber cuvette assembly 50 is shown having a transparent cuvette-inlet tube 52, aliquot extraction ports 54 and 56 to conductivity sensor modules (not labelled), heat-exchange radiators 58, a spectral sensor unit 60 (with parallel-mounted, line-of-sight source and detector), a light source 62 (e.g., an LED light source), an oxygen sensor light-guide holder 64, and a transparent cuvette-outlet tube 66. FIG. 3B depicts an exploded view of the independently-controllable, multi-chamber cuvette of FIG. 3A with its internal componentry exposed, according to embodiments of the present invention. Multi-chamber cuvette assembly 50 is shown further having a lower aliquot-level sensor 68, an upper aliquot-level sensor 70, Peltier heating elements 72 (for at least one independently-controllable measurement zone), thermal-contact windows 74 (for at least one independently-controllable measurement zone), temperature sensor PCBs 76 (printed circuit boards for at least one independently-controllable measurement zone), a cuvette body 78, a cuvette body support 80, and cuvette optical windows 82 (for each independently-controllable measurement zone).

Elaborating on how a liquid sample is collected, internally transferred, analyzed, and ejected from the portable multi-chamber analyzer, sample processing starts when an aliquot is initially drawn upwards into the device through small tubes inside multi-capillary aliquot-collection tube 2 (of FIGS. 1 and 2) by aliquot syringe pump 36 and syringe-pump linear actuator 42 (of FIG. 2A-D), which utilize negative pressure to enable the aliquot to be drawn up into transparent cuvette-inlet tube 52. The volume of the aliquot is measured as it passes lower aliquot-level sensor 68 (e.g., an optical sensor). The aliquot is further drawn upwards, entering and filling multiple, independently-controllable measurement zones in multi-chamber cuvette assembly 50, until the aliquot reaches upper aliquot-level sensor 70. At this point, aliquot collection is complete.

The entire aliquot in multi-chamber cuvette assembly 50 can then be drawn up into degasser chamber body 30 via transparent cuvette-outlet tube 66 for pre-processing of the aliquot using a liquid agitator (e.g., piezoelectric/ultrasonic vibration mechanism) to remove bubbles and various gases from the aliquot. The hydrostatic pressure maintained by aliquot syringe pump 36 and syringe-pump linear actuator 42 allows the aliquot to then be returned down into multi-chamber cuvette assembly 50 for analysis. Once the aliquot has returned to cuvette body 78, such dynamic control of aliquot movement further enables a type of agitated mixing of the individual portions of the aliquot in each independently-controllable measurement zone by rapidly oscillating syringe-pump linear actuator 42 to create an up-and-down "shaking" of each aliquot portion. While the entire aliquot represents a continuous volume of fluid, the aliquot portions can be largely "isolated" from each other by intervening narrow conduits (not shown in the drawings) between each measurement zone. Furthermore, maintaining hydrostatic pressure of the aliquot prevents fluid flow from measurement zone to measurement zone.

Multi-chamber cuvette assembly 50 is configured to provide access to a variety of sensors (described above) for measuring chemometric and/or spectroscopic parameters of the aliquot present in the measurement zones. At least one measurement zone of multi-chamber cuvette assembly 50 is independently-controllable via Peltier heating elements 72 and heat-exchange radiators 58 by conducting heat through thermal-contact windows 74 and temperature sensor PCBs 76 for controlling and regulating temperature, respectively, for accurate temperature adjustment. A temperature differential between neighboring measurements zones of up to about 100° C. can be achieved. Cuvette body 78 of multi-chamber cuvette assembly 50 provides access to spectral analyzers 38, 44, and 60, as well as light source 62 via cuvette optical windows 82.

Portions of the aliquot can also pass through aliquot extraction ports 54 and 56 to conductivity sensor modules to satisfy light path requirements in order to obtain optimal measurements. Solid samples can also be analyzed as dry material via solid-sample analysis compartment 12 (of FIG. 1A) with light-based sensors measuring in reflectance mode.

FIG. 4A depicts a planar view of the independently-controllable, multi-chamber cuvette assembly of FIG. 3A, according to embodiments of the present invention. FIG. 4B depicts a planar "cross-sectional cutaway" view of the independently-controllable, multi-chamber cuvette assembly of FIG. 4A with the cuvette inner-cavity volume exposed, according to embodiments of the present invention. The cross-section of multi-chamber cuvette assembly 50 reveals a cuvette inner-cavity volume 90 which contains the aliquot to be analyzed during operation. When the aliquot has been fully analyzed, it can be quickly and conveniently ejected from multi-chamber cuvette assembly 50 via aliquot syringe pump 36 and syringe-pump linear actuator 42 by applying a positive pressure to actively eject the aliquot from multi-capillary aliquot-collection tube 2. A similar process can be used to rapidly purge and clean cuvette inner-cavity volume 90 with a suitable solvent prior to collection of a subsequent aliquot. Alternatively, cuvette inner-cavity volume 90 can be purged by a secondary outlet port (not shown) for collection and/or further analysis, rather than being ejected through multi-capillary aliquot-collection tube 2.

FIG. 4C depicts a planar "90-degree rotated" view of the independently-controllable, multi-chamber cuvette assembly of FIG. 4A, according to embodiments of the present invention. FIG. 4D depicts a planar "cross-sectional cutaway" view of the independently-controllable, multi-chamber cuvette assembly of FIG. 4C with the cuvette inner-cavity volume exposed, according to embodiments of the present invention.

FIG. 5A depicts the planar view of the independently-controllable, multi-chamber cuvette assembly of FIG. 4A with a schematic representation of the optical paths employed during spectral analyses superimposed, according to embodiments of the present invention. FIG. 5A shows an upper aliquot-level sensor optical path I, spectral sensor optical paths II-V, and a lower aliquot-level sensor optical path VI. An oxygen sensor optical path VII is depicted as being perpendicular to the drawing plane (operative in reflectance mode). Optical paths I-VI are depicted in transmission mode for all spectral absorption measurements. Note that optical paths IV and V are co-located in the same measurement zone.

FIG. 5B depicts the planar view of the independently-controllable, multi-chamber cuvette assembly of FIG. 4C with a schematic representation of the optical paths employed during spectral analyses superimposed, according to embodiments of the present invention. FIG. 5B shows optical paths II and III (depicted as perpendicular to the drawing plane), oxygen sensor optical path VII, and spectral sensor optical paths VIII and IX (also depicted as being co-located in the same measurement zone). Optical paths VII-IX are depicted in reflectance mode.

FIG. 6A depicts a planar "120-degree sector" view of the cuvette inner-cavity volume depicted in FIGS. 4B and 4D with a schematic representation of the optical paths employed during spectral analyses superimposed, according to embodiments of the present invention. Cuvette inner-cavity volume 90 is shown with transmission optical paths I-VI superimposed.

FIG. 6B depicts an alternate, planar "120-degree sector" view of the cuvette inner-cavity volume depicted in FIGS. 4B and 4D with a schematic representation of the optical paths employed during spectral analyses superimposed, according to embodiments of the present invention. Cuvette inner-cavity volume 90 is shown with transmission optical path II (depicted as perpendicular to the drawing plane) and reflectance optical paths VII-IX superimposed. FIG. 6C depicts an alternate, planar "120-degree sector" view of the cuvette inner-cavity volume depicted in FIGS. 4B and 4D, according to embodiments of the present invention.

Figure 7:
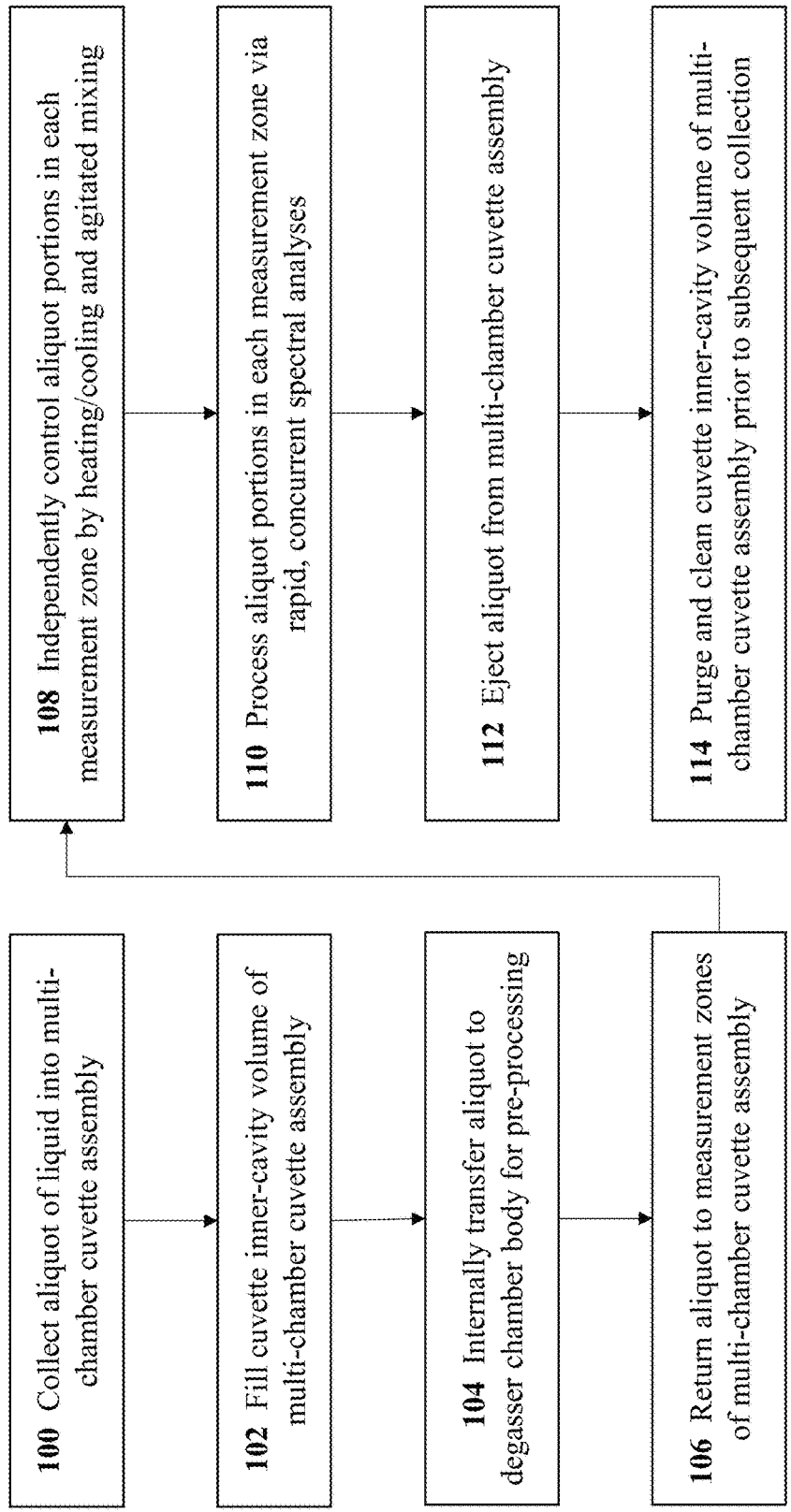
FIG. 7 is a simplified flowchart of the major process steps for aliquot processing of a liquid in the portable multi-chamber analyzer of FIGS. 1-6, according to embodiments of the present invention.

FIG. 7 is a simplified flowchart of the major process steps for aliquot processing of a liquid in the portable multi-chamber analyzer of FIGS. 1-6, according to embodiments of the present invention. Sample processing starts with an aliquot being drawn up into multi-chamber cuvette assembly 50 of the portable multi-chamber analyzer (Step 100). The aliquot collection is complete when it is detected to fill cuvette inner-cavity volume 90 of multi-chamber cuvette assembly 50 (Step 102). The aliquot is then internally transferred to degasser chamber body 30 for pre-processing (Step 104).

The aliquot is then returned to the measurement zones of multi-chamber cuvette assembly 50 (Step 106). Each aliquot portion in the measurement zones can be independently controlled by heating/cooling and agitated mixing (Step 108). The aliquot portions are then processed via rapid, concurrent spectral analyses (Step 110). The aliquot is then ejected from multi-chamber cuvette assembly 50 of the portable multi-chamber analyzer (Step 112). Cuvette inner-cavity volume 90 of multi-chamber cuvette assembly 50 can then be purged and cleaned with a solvent prior to subsequent aliquot collection (Step 114).

While the present invention has been described with respect to a limited number of embodiments, it will be appreciated that many variations, modifications, equivalent structural elements, combinations, sub-combinations, and other applications of the present invention may be made.

What is claimed is:

1. A device for rapid, concurrent spectral analyses, the device comprising:
   (a) an independently-controllable, multi-chamber cuvette having at least two contiguous analysis chambers forming a single continuous inner cavity configured to contain a liquid in an inner-cavity volume, wherein said independently-controllable, multi-chamber cuvette has a lower aliquot level positioned below said at least two contiguous analysis chambers and an upper aliquot level positioned above said at least two contiguous analysis chambers, wherein each said analysis chamber is configured to serve as an independently-controllable measurement zone for said liquid in said single continuous inner cavity when said inner-cavity volume is completely filled with said liquid, between said lower aliquot level and said upper aliquot level, by regulation of hydrostatic pressure in said single continuous inner cavity, when operational, in order to prevent fluid flow from a first given said analysis chamber to a second given said analysis chamber, and wherein each volume of said liquid in each said independently-controllable measurement zone is designated as an independent zone volume;
   (b) thermal-contact windows, suitably positioned in at least one said analysis chamber to provide adequate thermal contact to said at least one analysis chamber, adapted to enable independent temperature control of said at least one independent zone volume, when operational, in said at least one independently-controllable measurement zone; and
   (c) cuvette optical windows, suitably positioned in said each analysis chamber to provide independent optical access to said each independently-controllable measurement zone, adapted to enable chemometric and/or spectroscopic analysis of said each independent zone volume, when operational, in said each independently-controllable measurement zone.

2. The device of claim 1, wherein said cuvette optical windows are configured to define more than one optical path in at least one said independently-controllable measurement zone.

3. The device of claim 1, the device further comprising:
   (d) ancillary device components, wherein said ancillary device components are at least two items selected from the group consisting of:
      (i) an aliquot-collection tube positioned below said lower aliquot level for collecting and ejecting an aliquot of said liquid into said inner-cavity volume;
      (ii) a hydrostatic-pressure control mechanism positioned above said upper aliquot level for maintaining said hydrostatic pressure;
      (iii) a hydrostatic-pressure control actuator for performing said regulation and for actuating movement of said aliquot in said inner-cavity volume;
      (iv) a lower aliquot-level sensor for determining said lower aliquot level in said inner-cavity volume;
      (v) an upper aliquot-level sensor for determining said upper aliquot level in said inner-cavity volume;
      (vi) a degasser for uniformly degassing said aliquot;
      (vii) at least two heating/cooling elements suitably positioned in said each analysis chamber for regulating said independent temperature control in said each independently-controllable measurement zone;
      (viii) at least two heat-exchange radiators suitably positioned in said each analysis chamber for regulating said independent temperature control in said each independently-controllable measurement zone;
      (ix) at least one sensor light-guide for performing said chemometric analysis;
      (x) at least one conductivity sensor for performing said chemometric analysis;
      (xi) an oxygen sensor for analyzing said aliquot;
      (xii) at least one spectral sensor unit with parallel-mounted, line-of-sight source and detector for performing said spectroscopic analysis;
      (xiii) at least one light source for performing said spectroscopic analysis;
      (xiv) at least two spectral analyzers for performing said spectroscopic analysis; and
      (xv) a solid-sample analysis compartment for performing said spectroscopic analysis in reflectance mode on solid samples.

4. The device of claim 3, wherein said hydrostatic-pressure control mechanism is a syringe pump and said hydrostatic-pressure control actuator is a syringe-pump linear actuator.

5. The device of claim 3, wherein said movement of said aliquot includes a type of agitated mixing of said aliquot in each independently-controllable measurement zone by rapidly oscillating said hydrostatic-pressure control actuator to create an up-and-down shaking of said aliquot in said cuvette inner-cavity volume.

6. The device of claim 3, wherein said at least two spectral analyzers are independently operational in a near-infrared spectral region in transmission and/or reflectance mode.

7. A method for performing rapid, concurrent spectral analyses, the method comprising the steps of:
   (a) collecting an aliquot of liquid by drawing up said aliquot into a multi-chamber cuvette assembly, wherein said multi-chamber cuvette has a lower aliquot level and an upper aliquot level;
   (b) filling a cuvette inner-cavity volume positioned between said lower aliquot level and said upper aliquot level of said multi-chamber cuvette assembly;

(c) internally transferring said aliquot to a degasser chamber body for pre-processing;
(d) returning said aliquot to at least two measurement zones in said cuvette inner-cavity volume of said multi-chamber cuvette assembly, wherein said lower aliquot level is positioned below said at least two measurement zones and said upper aliquot level is positioned above said at least two measurement zones;
(e) independently controlling aliquot portions in at least one said measurement zone by heating, cooling, and/or agitated mixing, wherein said agitated mixing is created by rapidly oscillating said aliquot to cause an up-and-down shaking of said aliquot in said cuvette inner-cavity volume;
(f) processing said aliquot portions in each said measurement zone by performing concurrent spectral analyses;
(g) ejecting said aliquot from said multi-chamber cuvette assembly; and
(h) purging and cleaning said cuvette inner-cavity volume of said multi-chamber cuvette assembly prior to subsequent collection.

\* \* \* \* \*